United States Patent
Gulbrandsen et al.

(10) Patent No.: US 6,610,885 B1
(45) Date of Patent: Aug. 26, 2003

(54) PROCESS FOR THE PREPARATION OF CONTRAST AGENTS

(75) Inventors: Trygve Gulbrandsen, Oslo (NO); Odd Einar Ingvoldstad, Oslo (NO); Lars Terje Holmaas, Oslo (NO)

(73) Assignee: Amersham Health AS, Olso (NO)

( * ) Notice: Subject to any disclaimer, the term of this patent is extended or adjusted under 35 U.S.C. 154(b) by 0 days.

(21) Appl. No.: 09/098,350

(22) Filed: Jun. 17, 1998

Related U.S. Application Data

(63) Continuation of application No. 08/845,134, filed on Apr. 21, 1997, now Pat. No. 5,840,967.
(60) Provisional application No. 60/029,143, filed on Oct. 21, 1996.

(30) Foreign Application Priority Data

Aug. 29, 1996 (GB) .............................................. 9618055

(51) Int. Cl.$^7$ ............................................ C07C 233/05
(52) U.S. Cl. ...................................................... 564/153
(58) Field of Search ......................................... 564/153

(56) References Cited

U.S. PATENT DOCUMENTS 4,250,113 A    2/1981    Nordal et al. ............... 564/153
5,847,212 A    12/1998   Wang et al.

FOREIGN PATENT DOCUMENTS

| DE | 2 216 627  | 4/1972  |
| DE | 27 26 196  | 6/1977  |
| EP | 0 105 752  | 4/1984  |
| EP | A-1 105 752 | 4/1984 |
| EP | A-1 108 638 | 5/1984 |
| GB | 1 374 918  | 11/1974 |
| GB | A-1 548 594 | 7/1979 |
| WO | 85/01727   | 4/1985  |
| WO | 87/00757   | 2/1987  |

OTHER PUBLICATIONS

Kjemi No. 6/90 pp. 6–8, Gulbrandsen T.

*Primary Examiner*—Paul J. Killos
(74) *Attorney, Agent, or Firm*—Bacon & Thomas

(57) ABSTRACT

Process for the preparation of contrast agents The invention provides a process for the preparation of an N-alkyl-acylamino-phenyl-carboxylic acid or carboxylic acid derivative by liquid phase acylation and subsequent N-alkylation of a corresponding amino-phenyl-carboxylic acid (or carboxylic acid derivative), the improvement comprising the addition of an alkylating agent to a solution containing the reaction products of said acylation, to effect said N-alkylation.

6 Claims, No Drawings

US 6,610,885 B1

PROCESS FOR THE PREPARATION OF CONTRAST AGENTS

CROSS REFERENCE TO RELATED APPLICATIONS

This application is a continuation of application Ser. No. 08/845,134, now U.S. Pat. No. 5,840,967, filed Apr. 21, 1997 which claims benefit of provisional application serial No. 60/029,143 filed Oct. 21, 1996.

FIELD OF THE INVENTION

The invention relates to a process for the preparation of iodinated X-ray contrast agents, in particular non-ionic N-alkylated-acylamino-triiodophenyl compounds such as iohexol, iodixanol, iopentol and ioxilan.

BACKGROUND OF THE INVENTION

Non-ionic iodinated X-ray contrast agents have achieved great commercial success over the past twenty years and accordingly improving the efficiency of their manufacture is of great importance.

The manufacture of non-ionic contrast agents includes production of the chemical drug substance (primary production), followed by formulation to drug product (secondary production). The drug substance is usually made in a multistep chemical synthesis, and is thoroughly purified before formulation. As with any commercial drug production it is important to optimize yield, process time and demand for expensive equipment. All these parameters depend both on the chemical reaction conditions and the work-up between each step. The number of steps in the overall synthesis will of course be of great importance and if the work-up between individual process steps could be omitted significant improvement in efficiency can be obtained, provided that sufficient quality and yield are maintained for the final product.

Omitting the work-up between two process steps means that the second step will be performed in the crude reaction solution resulting from the previous step. Potential major advantages includes:

higher yield (through avoidance of loss of the intermediate in the work-up);

elimination of isolation, purification, drying and analysis of the intermediate;

significant reduction in equipment demand (eg. reactors, filters, driers, etc.); and significant reduction of the process time.

Despite these potential advantages, in practice intermediates are usually worked up between successive process steps. The reasons for this often include the facts that impurities may carry through the process and that the optimum solvent for the first reaction is usually not the same as for the second reaction.

The present multistage preparation of certain non-ionic X-ray contrast agents requires successive acylation and N-alkylation reactions. Thus for example in the production of iohexol (as described in SE-7706792-4 and by Gulbrandsen in Kjemi No. 6/90, pages 6–8), 5-amino-N,N'-bis(2,3-dihydroxypropyl)-2,4,6-triiodophthalamide (hereinafter 5-Amine) is acetylated to produce 5-acetamido-N,N'-bis(2,3-dihydroxypropyl)-2,4,6-triiodophthalamide (hereinafter 5-Acetamide) which is then N-alkylated to produce 5-[N-(2,3-dihydroxypropyl)-acetamido]-N,N'-bis(2,3-dihydroxypropyl)-2,4,6-triiodophthalamide (iohexol).

Similarly, in the production of iopentol as described in NO-160918, 5-Amine is acetylated to yield 5-Acetamide which is N-alkylated to produce 5-[N-(2-hydroxy-3-methoxypropyl)acetamido-N,N'-bis(2,3-dihydroxypropyl)-2,4,6-triiodophthalamide (iopentol).

In the production of iodixanol described in NO-161368, 5-Amine is acetylated to yield 5-Acetamide which is then reacted with a bifunctional alkylating agent, a coupling agent, to yield 1,3-bis(acetamido)-N,N'-bis[3,5-bis(2,3-dihydroxypropylaminocarbonyl)-2,4,6-triiodophenyl]-2-hydroxypropane (iodixanol).

In the preparation of iohexol described above, the acylation is effected in acetic anhydride in the presence of a catalytic amount of sulphuric acid followed by concentration and addition of methanol. Thereafter water and sodium hydroxide (to pH 10–11) are added, base hydrolysis (to remove O-acyl groups) proceeds for 4–5 hours and 5-Acetamide is isolated from the reaction mixture by cooling and neutralization with hydrochloric acid. The precipitated 5-Acetamide is filtered, washed with water and dried. The 5-Acetamide is then dissolved in propylene glycol with the addition of sodium methoxide, the resulting methanol is stripped off and the N-alkylating agent (1-chloro-2,3-propanediol) is added. After the N-alkylation reaction is complete, the reaction mixture is evaporated to dryness and further purification steps (involving crystallization from a further solvent, butanol) are performed to yield the purified iohexol in a form suitable for use in secondary production.

The 5-Amine to 5-Acetamide acylation described for the preparation of iopentol in NO-160918 is similar, with the 5-Amine being acylated in acetic anhydride in the presence of a catalytic amount of p-toluene sulphonic acid. After cooling the reaction mixture, a precipitate forms which is filtered off and suspended in a mixture of methanol and water and hydrolysed under basic conditions (pH 11.5). The 5-Acetamide product is filtered off after cooling to ambient temperature, neutralization with HCl and further cooling to 30° C. The 5-Acetamide is washed with water and dried before being suspended in propylene glycol. Sodium hydroxide is added and when all solid material has dissolved, the N-alkylating agent (here 1-chloro-3-methoxy-2-propanol) is added. After the alkylation is quenched, several purification steps are again required before satisfactorily pure iopentol is obtained.

For the synthesis of iodixanol described in NO-161368, 5-Acetamide is prepared and worked up as described for iopentol above. It is then suspended in water and dissolved therein with the addition of sodium hydroxide. The N-alkylating agent, the coupling reagent epichlorohydrin, is then added. After the reaction is complete it is quenched with dilute hydrochloric acid and further purification steps are carried out in order to obtain satisfactorily pure iodixanol.

SUMMARY OF THE INVENTION

It has now been surprisingly found that the work-up of the 5-Acetamide before the subsequent N-alkylation may be avoided without unacceptable loss in yield or purity of the acylated, N-alkylated product and without undue complication of the purification procedure for that product.

Thus viewed from one aspect the invention provides a process for the preparation of an N-alkyl-acylamino-phenyl-carboxylic acid or carboxylic acid derivative by liquid phase acylation and subsequent N-alkylation of a corresponding amino-phenyl-carboxylic acid (or carboxylic acid derivative) characterised in that said N-alkylation is effected by addition of an alkylating agent to a solution containing the reaction products of said acylation, ie. those that remain in solution during the liquid phase acylation.

Viewed from an alternative aspect the invention provides a process for the preparation of an N-alkyl-acylamino-phenyl-carboxylic acid or carboxylic acid derivative compound comprising acylating an amino-phenyl-carboxylic acid (or carboxylic acid derivative) in a liquid phase, base hydrolysing the acylated product to remove O-acyl groups from the N-acyl-amino intermediate and, maintaining the liquid phase at a basic pH, N-alkylating the N-acylamino intermediate.

DETAILED DESCRIPTION OF THE INVENTION

In the process of the invention, the aminophenyl carboxylic acid or carboxylic acid derivative starting product is preferably a compound having a total of three amino and carboxyl groups on the phenyl ring, eg. an aminoisophthalic acid or derivative or a diaminobenzoic acid or derivative. By carboxylic acid derivative is meant for example a salt, ester or amide, eg. an CONHR* or COOR* group where R* is optionally hydroxylated alkyl preferably optionally hydroxylated $C_{1-6}$ alkyl. Furthermore the starting compound is preferably a triiodophenyl compound, particularly an alkylamino-carbonyl-triiodophenyl compound and most particularly a 2,4,6-triiodo-2,5-bis(alkylamino-carbonyl)-aniline, such as 5-Amine for example. The alkyl moiety of any alkylaminocarbonyl group will preferably carry one or more hydroxyl groups and will typically contain up to 6, preferably up to 4 carbon atoms.

The acylation of the starting compound may be effected using any convenient acylating agent, eg. an acetylating agent such as for example an acid halide or more preferably acetic anhydride.

Following the acylation, which is conveniently acid catalysed, the product is base hydrolysed, eg. at pH 11 to 12, to remove unwanted O-acyl groups without displacing the desired N-acyl groups. Base hydrolysis may be with any organic or inorganic base but is preferably effected using an inorganic base, eg. an alkali metal hydroxide such as sodium hydroxide.

After the base hydrolysis, the solution pH is if necessary adjusted to an appropriate basic value for N-alkylation (generally within the range 10–12), and if desired further solvent (eg. a lower alcohol such as a $C_{1-4}$ alcohol, eg. methanol, optionally together with water) is added to the reaction mixture before, during or after addition to the reaction mixture of the alkylating agent, thereby ensuring that the non-isolated intermediate does not precipitate out.

Thus unlike prior successive acylation and N-alkylation reactions, the reaction medium is maintained at a basic pH and the N-acylated product (and the by-products) are not isolated from the reaction mixture before the subsequent N-alkylation step.

The N-alkylating agent used in the N-alkylation of the non-isolated intermediate may be any alkylating agent capable of introducing the desired alkyl group (or a precursor for a desired group) at the acylamino nitrogen. Where the acylated, N-alkylated product is intended to be a dimer (ie. containing two iodophenyl groups), the alkylating agent may be a bifunctional coupling agent.

For the preparation of iohexol, 1-halo-2,3-propanediols (eg. 1-chloro-2,3-propanediol) and glycidol are preferred alkylating agents. For the preparation of iopentol, 1-halo-3-methoxy-2-propanols (eg. 1-chloro-3-methoxy-propanol) are preferred. For the production of iodixanol a coupling agent such as a 1,3-halo-2-propanol or more preferably epichlorohydrin may be used.

The alkylation reaction may be terminated conventionally by quenching with acid, eg. HC1, and the acetylated, N-alkylated product may also be worked up conventionally, eg. by crystallization from an appropriate solvent or solvent mixture, eg. one or more $C_{1-6}$ alcohols.

Where the N-alkyl-acylamino product is a product such as iohexol, iopentol or iodixanol, this work-up yields a product which can be used for secondary production of an X-ray contrast medium. However for other end products, the product may be used as the starting material for further synthetic steps, eg. in the primary production of a non-ionic X-ray contrast agent.

Thus the process of the present invention allows N-acylation and N-alkylation to be effected as a one-pot synthesis achieving savings in equipment, time and materials without undue loss in yield and, surprisingly, achieving in the purification of the end product comparable or better purity levels to those achieved when the intermediate and the end product are both subject to work up stages.

The process of the present invention is particularly applicable to the preparation of the following N-alkyl-acylaminophenyl X-ray contrast agents: iomeprol, ioversol, ioxilan, iotrolan, ioxaglate, iodecimol, 2-iopyrol, 2-iopiperidol, iohexol, iopentol and iodixanol.

The invention will now be illustrated further by reference to the following non-limiting Examples.

EXAMPLE 1

5-Amino-N,N'-bis(2,3-dihydroxypropyl)-2,4,6-triiodoisophthalamide (388 g), acetic anhydride (838 g) and p-toluene sulfonic acid (2 g) were mixed and heated to reflux for 1.5 hours, before concentration to a highly viscous solution under reduced pressure. Methanol (44 g) was added to the solution in several portions with distillation under atmospheric pressure between each addition, followed by a final portion of methanol (266 g). A small amount of distilled water (40 ml) was added before stirring at 55° C. overnight.

A portion (490 ml) of a solution made as described above was added to a jacketed reactor at about 30° C., and stirred with a speed of 150 rpm. The pH was raised by aqueous sodium hydroxide (50 w/v %, 190 ml) to about 12. 1-Chloro-2,3-propanediol (49 g) was added to the solution, and the pH was further adjusted by sodium hydroxide (50 w/v %, 25 ml) to about 11.5. Small amounts of additional 1-chloro-2,3-propanediol (total 6 ml) were added during the first 24 hours of the reaction. After a total reaction time of 99 hours, the solution was analyzed by reversed phase HPLC (water/acetonitrile as eluent) with the following results:

| | |
|---|---|
| Iohexol | 94.4% |
| 5-Acetamide | 1.9% |
| 5-Amine | 0.6% |
| Other impurities | 3.1% |

EXAMPLE 2

5-Amino-N,N'-bis(2,3-dihydroxypropyl)-2,4,6-triiodoisophthalamide (388 g), acetic anhydride (838 g) and p-toluene sulfonic acid (2 g) were mixed and heated to reflux for 1.5 hours, before concentration to a highly viscous solution under reduced pressure. Methanol (44 g) was added to the solution in several portions with distillation under atmospheric pressure between each addition, followed by a final portion of methanol (266 g). A small amount of distilled water (40 ml) was added before stirring at 55° C. overnight.

A portion (490 ml) of a solution made as described above was added to a jacketed reactor at about 35° C., and stirred with a speed of 150 rpm. The pH was raised by aqueous sodium hydroxide (50 w/v %, 200 ml) to about 12. Additional sodium hydroxide solution (10 ml) and 1-chloro-3-methoxy-2-propanol (42 g) were added, and the pH was adjusted back to about 12 by small amounts of sodium hydroxide solution. Further additions of 1-chloro-3-methoxy-2-propanol (total 21 g) were added after 2, 3, 4, 5 and 6 hours of reaction. After a total reaction time of 53 hours, the mixture was analyzed by HPLC (water/acetonitrile as eluent) with the following results:

| | |
|---|---|
| Iopentol | 91.4% |
| 5-Acetamide | 1.6% |
| 5-Amine | 0.3% |
| Other impurities | 6.8% |

What is claimed is:

1. A process for the preparation of iohexol comprising the steps of:

(a) forming a reaction mixture containing 5-acetamido N,N'-bis(2,3-dihydroxypropyl)-2,4,6-triodoisophthalamide, a base, a solvent and glycidol, (b) N-alkylating said 5-acetamido compound with the glycidol to form iohexol, and (c) isolating iohexol.

2. The process of claim 1 in which the base is an inorganic base.

3. The process of claim 1 in which the base is an alkali metal hydroxide.

4. The process of claim 1 in which the base is sodium hydroxide.

5. The process of claim 1 in which the reaction temperature in step (b) is maintained at 30° C.

6. The process of claim 1 in which the iohexol is isolated by crystallization from a $C_{1-6}$ alcohol.

* * * * *